United States Patent [19]

Beu

[11] Patent Number: 4,836,779
[45] Date of Patent: Jun. 6, 1989

[54] DENTAL FACE BOW

[75] Inventor: Richard A. Beu, Eggertsville, N.Y.

[73] Assignee: Teledyne Hanau, Buffalo, N.Y.

[21] Appl. No.: 181,987

[22] Filed: Apr. 15, 1988

Related U.S. Application Data

[63] Continuation-in-part of Ser. No. 57,540, Jun. 2, 1987, abandoned.

[51] Int. Cl.⁴ ............................................. A61C 19/04
[52] U.S. Cl. .................................................... 433/73
[58] Field of Search ..................... 433/54, 55, 56, 57, 433/58, 59, 60, 61, 75

[56] References Cited

U.S. PATENT DOCUMENTS

| | | |
|---|---|---|
| 497,122 | 5/1893 | Garretson . |
| 1,188,416 | 6/1916 | Dalbey . |
| 1,211,254 | 1/1917 | Snow . |
| 1,402,225 | 1/1922 | Garretson . |
| 2,579,111 | 12/1951 | Fleischhacker ........................ 32/20 |
| 3,206,852 | 9/1965 | Swanson ............................. 32/32 |
| 3,307,262 | 3/1967 | Chaiken ............................. 32/19 |
| 3,866,323 | 2/1975 | Granger ............................. 32/14 |
| 4,330,277 | 5/1982 | Beu .................................. 433/73 |
| 4,695,252 | 9/1987 | Edwardson ........................ 433/73 |

Primary Examiner—Robert Peshock
Attorney, Agent, or Firm—Michael L. Dunn

[57] ABSTRACT

A dental face bow comprising a U-shaped spring member including two opposing uniformly acting spring biased legs and a central portion. The U-shaped spring member has a cross section with vertical and horizontal cross sectional axes. The vertical axis is at least twice the length of the horizontal axis. The bow includes two inwardly extending earpieces, proximate the ends of the legs, adapted to fit the external acoustic meatuses of a dental patient. A bite plate for holding a material in contact with oral structures of a dental patient and adjusting means for rigidly securing said bite plate in a fixed relationship with said earpieces are provided.

7 Claims, 2 Drawing Sheets

DENTAL FACE BOW

BACKGROUND OF THE INVENTION

This is a continuation-in-part of copending patent application Ser. No. 057,540 filed June 2, 1987 now abandoned.

This invention relates to a dental face bow which is useful to record relationships between a dental patient's dentition and parts of his skull and jaw structure, and to transfer such to a dental articulator. More particularly, this invention relates to a readily fittable or positionable dental face bow wherein contact members thereof may be easily adjusted to position against a patient's head at a desired location.

Dental articulators have been employed in the design and finishing of prostheses to help improve the fitting thereof and to make them compatible with various human jaw movements. Dental face bows have also been employed to record and/or measure certain characteristics of a patient's dentition so that such characteristics can be accurately transferred to a dental articulator. However, before the present invention such face bows could not be as easily fitted to the patient by the dentist or dental technician. Additionally, various advantages or parts of preferred face bows of this invention were not hitherto attainable nor was the fixing in position of a bite plate with respect to the face bow and the articulator as easily effected.

Examples of such prior art dental face bows may, for example, be seen in numerous U.S. patents. Almost all of the face bows described in such patents are exceedingly complex and expensive to manufacture and additionally are difficult to use.

A few examples of the many patents illustrating such complex face bows are U.S. Pat. Nos. 4,330,277; 3,307,262; and 3,866,323. There are many other such patents. While attempts have been made to simplify the complexity of face bows, such attempts have not been successful because of unreliable accuracy and reproducibility on a dental articulator. Such an attempt is, for example, shown in U.S. Pat. No. 1,188,416 which utilizes a spring rather than the usual metered earpiece to obtain centering and reproducibility. U.S. Pat. No. 1,188,416 simply exchanges one complexity for another since once the earpieces 13 are spread apart they are retained by a complex retaining arrangement. Furthermore, the necessary slack at pivotal pins 12 and 16 make the bow inaccurate. U.S. Pat. No. 1,402,225 shows a chin retaining means as opposed to a face bow. Such a chin retaining means merely steadies the chin at a particular position while measurements or observations are made by other means. The chin retaining means of U.S. Pat. No. 1,402,225 has a complex spring arrangement secured by screws. There is almost certainly slack in the arrangement. U.S. Pat. No. 497,122 also describes a chin retaining device as opposed to a face bow. There is probably at least some loss of accurate retention as a result of slack in a racket and pawl arrangement.

U.S. Pat. No. 4,695,252 filed Dec. 5, 1985, discloses a face bow having a U shape and legs with the ability to spring outwardly. The legs of the bow have a round cross section and in general the patent makes it clear that earpieces are preferably adjustable and in fact are adjusted before the face bow is placed on a patient. The patent's only reference to the possibility of using the disclosed face bow without adjustable earpieces is made in column 3 lines 40–44 where it is stated, "Therefore, it could be quite possible to have ear pieces mounted in fixed relation to the bow means ends. However, the ear pieces 2 shown in FIG. 3 are displaceable on the end of the bow means between two extreme limits." The preferred embodiment of this patent is clearly not to use fixed earpieces and for good reason. This patent discloses no way to do so without either causing undue pressure upon patient meatuses or alternatively reducing the diameter of the circular cross section of the bow to unacceptably weak limits.

The inventor herein previously developed a spring operated face bow having a U-shaped unit made of spring steel wherein the earpieces were attached proximate the ends of the legs of the U and the holder for a bite plate was suspended from the center of the base of the U. This unit was experimentally tried as early as 1983 and found to be unsatisfactory. In particular, reproduction of the patient's dentition on a dental articulator was found to be insufficiently accurate.

BRIEF DESCRIPTION OF THE INVENTION

The invention is a dental face bow comprising:

(a) a U-shaped spring member including two opposing uniformly acting spring biased legs and a central portion, said U-shaped spring member having a cross section with vertical and horizontal cross sectional axes, said vertical axis being at least twice the length of the horizontal axis;

(b) two inwardly extending earpieces, proximate the ends of the legs, adapted to fit the external acoustic meatuses of a dental patient;

(c) a bite plate for holding a material in contact with oral structures of a dental patient; and (d) adjusting means for rigidly securing the bite plate in a fixed relationship with the earpieces, the adjusting means is suspended from a position on the central portion, which position is on a line perpendicular from the center of a line between the centers of the earpieces.

Desirably, the face bow further comprises an orbitale pointer horizontally movably positioned on one of said legs so that the pointer may be positioned to point at the orbitale of the dental patient.

The U-shaped spring member comprises a U-shaped piece of spring steel or other dimensionally stable spring material and is preferably, but not essentially, a unitary structure. In any case the terminal portions of the legs can be easily manually moved apart, i.e. less than one kilogram (2.2 pounds) and preferably less than one-half kilogram (1.1 pounds) of force to separate the legs far enough to move the earpieces into position to fit the acoustic meatuses, without adjustment of the earpieces on the legs, and less than one and preferably less than one-half kilogram of force when the earpieces are in place in the acoustic meatuses, for acoustic meatuses which are between 10 and 14 centimeters apart.

DETAILED DESCRIPTION OF THE INVENTION

Figure 1:
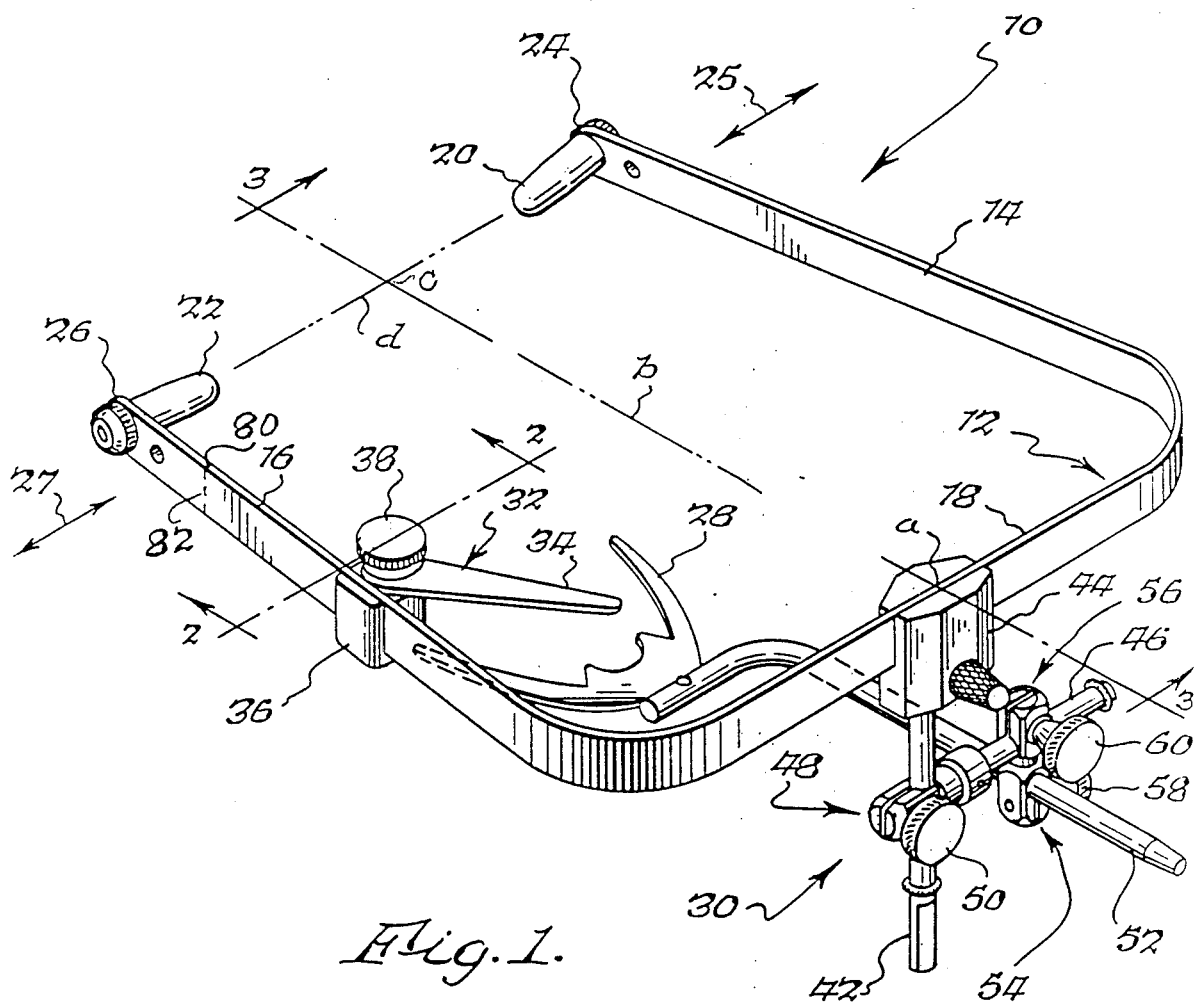
FIG. 1 is a perspective view of a preferred embodiment of the face bow of the invention.

The face bow of the present invention is much simpler than the best face bows of the prior art yet has comparable accuracy. This comparable accuracy results from several modifications of prior art face bow structure. In particular, the U-shaped spring member acts uniformly with uniform pressure in relation to the bite plate. This result occurs for several reasons including spring uniformity and stability, rigid securing of the bite plate in relationship to the earpieces and the securing of the bite plate by adjusting means suspended from a position on the central portion (base) of the U-shaped spring member where the position is on a line perpendicular from the center of a line between the centers of the earpieces. Low separating force and dimensional stability are simultaneously obtained by utilizing a spring member cross section wherein the vertical axis of the cross section is at least twice and preferably at least four times the length of the horizontal axis of the cross section. The vertical cross sectional axis is the longest cross sectional axis and is essentially vertical and essentially parallel the surface of the patients face when the patient is upright and the bow is in position on the patient and the horizontal cross sectional axis is essentially perpendicular to the vertical cross sectional axis and is essentially horizontal and essentially perpendicular to the surface of the patient's face when the patient is upright and the face bow is in position on the patient.

The above unique structure permits inward/outward movement of the earpieces, with a low uniform force, such that the relationship between the bite plate and the center of the distance between the earpieces remains constant. This permits use of the face bow on a patient with low meatuses pressure, without earpiece adjustment, and transfer to a dental articulator without compensation for the difference between the head thickness of the patient and the thickness of the articulator. Time consuming adjustments and/or calculations are thus eliminated.

A face bow made essentially in accordance with the teachings of U.S. Pat. No. 4,695,252 was compared with a face bow made in accordance with the present invention with respect to force required to separate the legs of the bow. The material of construction of the bow in accordance with U.S. Pat. No. 4,695,252 was wrought aluminum and was chosen to keep separation pressure as low as reasonably possible. The U.S. Pat. No. 4,695,252 circular cross section was selected at 0.635 cm (¼ inch) which was believed to be as low as practical to maintain vertical dimensional stability. The bow of the invention was made of stiffer spring steel and had a 0.16 cm (1/16 inch) horizontal cross sectional axis and a 1.27 cm (½ inch) vertical cross sectional axis.

The results of the comparison are as shown in Table 1.

TABLE 1

| | Distance Between Earpieces | Kilogram Force On Meatus |
|---|---|---|
| Bow of the Invention | 10 centimeters | 0 kg |
| | 11 centimeters | 0.156 kg |
| | 12 centimeters | 0.270 kg |
| | 13 centimeters | 0.370 kg |
| | 14 centimeters | 0.440 kg |
| | 15 centimeters | 0.525 kg |
| Bow of U.S. Pat. No. | 10 centimeters | 0 kg |
| | 11 centimeters | 1.193 kg |

TABLE 1-continued

| | Distance Between Earpieces | Kilogram Force On Meatus |
|---|---|---|
| 4,695,252 | 12 centimeters | 1.932 kg |
| | 13 centimeters | 2.841 kg |
| | 14 centimeters | 3.722 kg |
| | 15 centimeters | 4.205 kg |

A comparison of the forces upon the meatuses clearly shows the superiority of the bow of the present invention.

For a more detailed explanation of a preferred embodiment of the invention, reference may be had to the drawings. As best seen in FIG. 1, the face bow 10 comprises a U-shaped spring member 1 including two opposing uniformly acting spring biased legs 14 and 16 and a central or base portion 18. Two inwardly extending earpieces 20 and 22 are provided proximate the ends 24 and 26 of legs 14 and 16 for fitting the auditory or acoustic meatuses of a dental patient by moving legs 14 and 16, and attached earpieces 20 and 22 in the directions of arrows 25 and 27. The earpieces are preferably fixed with relation to the legs, i.e., non-adjustable. As can be readily seen in FIG. 1, vertical cross sectional axis 82 of legs 14 and 16 of member 12 is at least twice the length of horizontal axis 80 and is in fact over four times the length of horizontal axis 80.

A bite plate 28 is provided for holding a material in contact with oral structures of the dental patient. The material is usually a dental impression material. Adjusting means 30 is provided for rigidly securing bite plate 28 in a fixed relationship with earpieces 20 and 22. The adjusting means 30 is suspended from a position (a) on central portion 18. Position (a) is on a line b) which is perpendicular from the center (c) of line (d) between the centers of earpieces 20 and 22.

An orbitale pointer 32 is provided which is horizontally movably positioned on leg 16 so that pointer member 34 may be adjusted to point at the orbitale of the dental patient. Earpieces 20 and 22 in the auditory meatuses and pointer 32 at the orbitale of the dental patient together form a reference plane.

Figure 2:
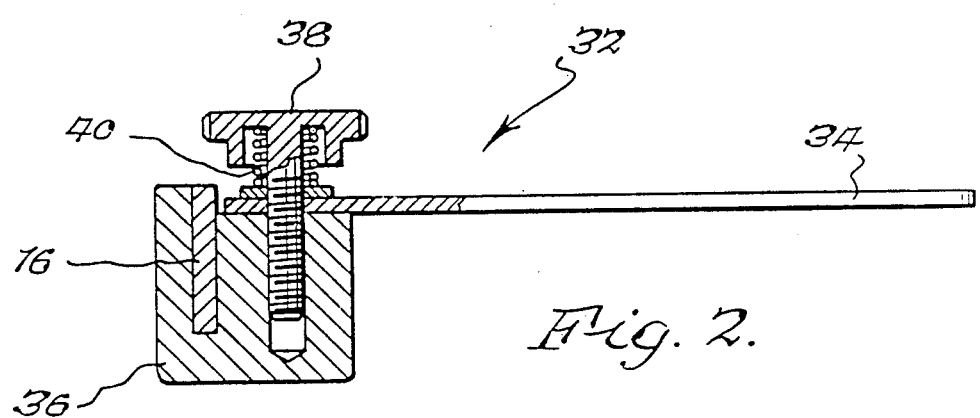
FIG. 2 is a cross-sectional view taken on line 2—2 of FIG. 1.

The orbitale pointer 32, as best seen in FIGS. 1 and 2 may comprise a pointer member 34 secured to leg 16 by means of a connecting block 36. Pointer member 34 is adjustably held to connecting block 36 by means of screw 38 and spring 40.

The U-shaped spring member 12 may be a unitary structure comprising a U-shaped piece of spring material such as spring steel or may optionally be legs 14 and 16 of spring material each rigidly secured at one and to a rigid base portion 18.

Figure 3:
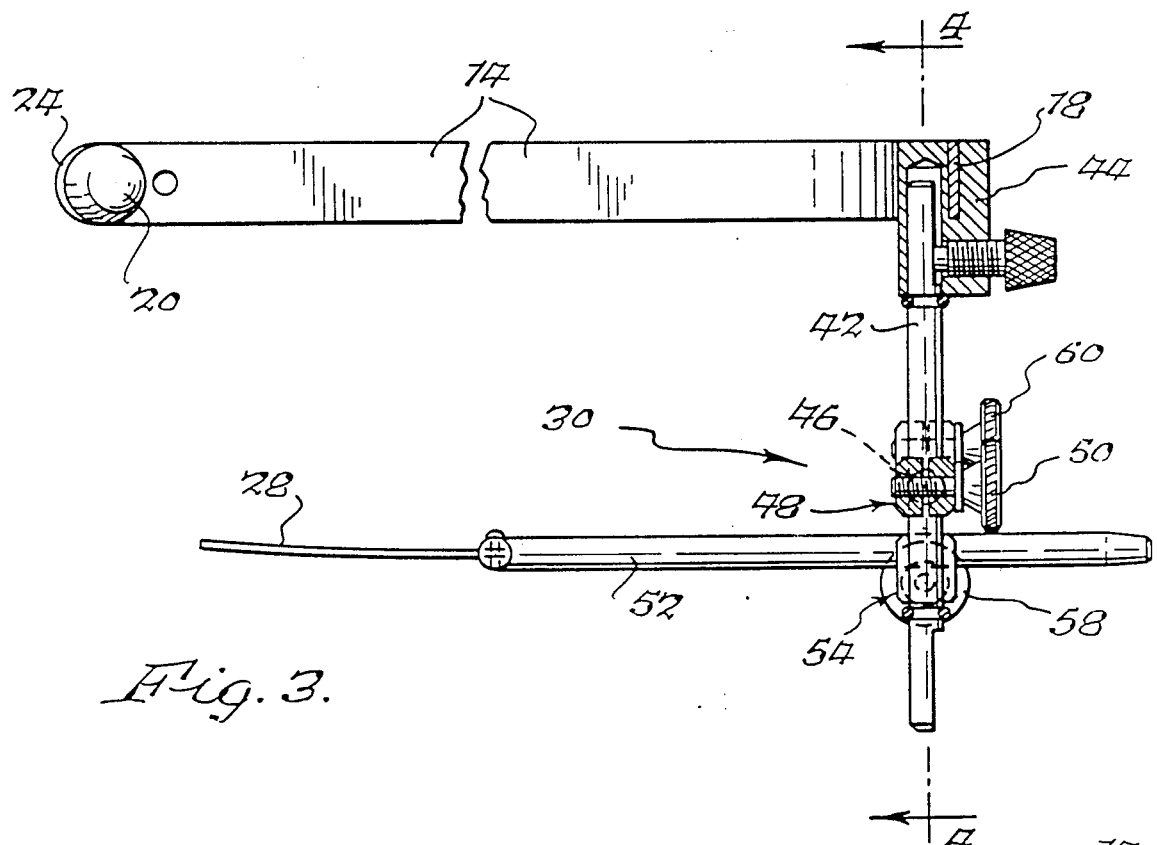
FIG. 3 is a cross-sectional view taken on line 3—3 of FIG. 1.
Figure 4:
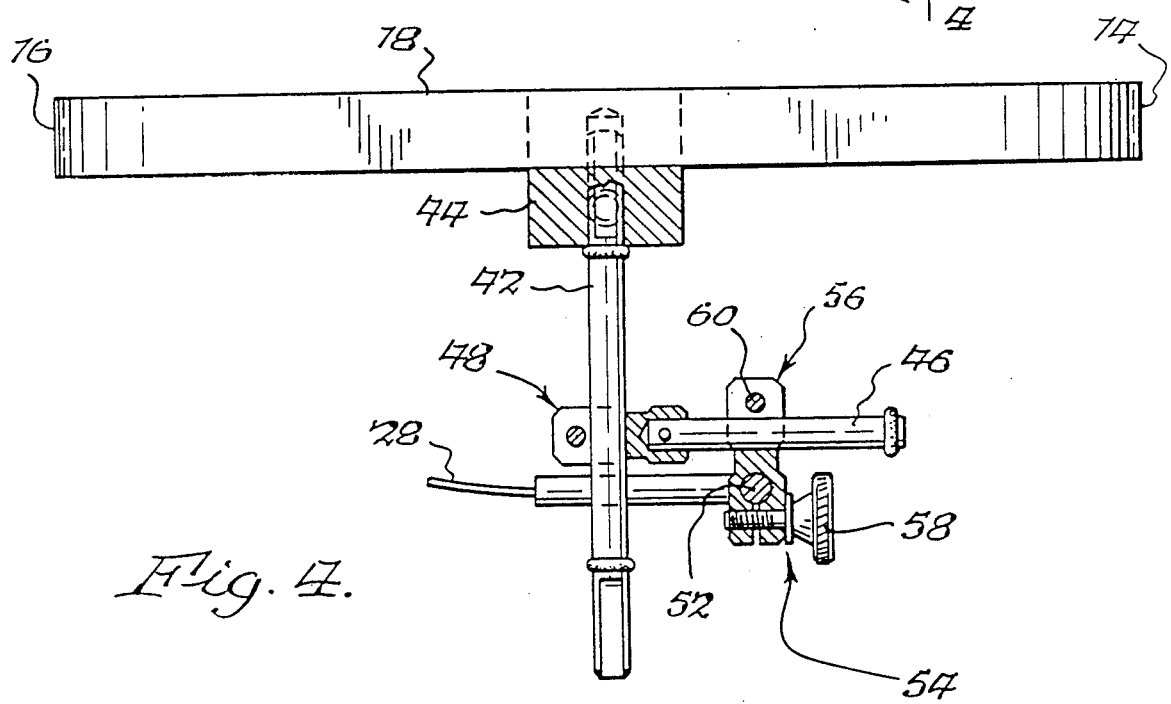
FIG. 4 is a cross-sectional view taken on line 4—4 of FIG. 3.

As best seen in FIGS. 1, 3 and 4, the adjusting means 30 may comprise a rigid transfer rod 42 securely perpendicularly attached to the central portion 18 of U-shaped spring member 12 by means of transfer rod rigid connecting block 44.

A rigid bar 46, essentially parallel to central portion 18 is adjustably rigidly connected, i.e., may be adjusted but when secured is rigidly connected, to transfer rod 42. The connection is adjustable to vary the distance between central portion 18 and rigid bar 46. The connection comprises a clamp means 48 and tightening screw 50.

A bite plate rod 52 is rigidly secured at one end to bite plate 28 and adjustably rigidly connected at the other end to rigid bar 46 by means of bite plate connector 54 which comprises dual clamp 56 and clamp screws 58 and 60. The bite plate connector 54 allows adjustment of bite plate 28 along a line parallel to rigid bar 46 and generally toward and away from line (d) between earpieces 20 and 22.

What is claimed is:

1. A dental face bow comprising:
   (a) a U-shaped spring member including two opposing uniformly acting spring biased legs and a central portion, said U-shaped spring member having a cross section with vertical and horizontal cross sectional axes, said vertical axis being at least twice the length of the horizontal axis;
   (b) two inwardly extending earpieces, proximate the ends of said legs, biased by the legs and adapted to fit the external acoustic meatuses of a dental patient, less than one-half kilogram of force being required at the earpieces to separate the earpieces by a distance of between 10 and 14 centimeters;
   (c) a bite plate for holding a material in contact with oral structures of a dental patient; and
   (d) adjusting means for rigidly securing said bite plate in a fixed relationship with said earpieces.

2. The dental face bow of claim 1 wherein the earpieces have a fixed relationship to the ends of said legs.

3. The face bow of claim 1 wherein said adjusting means is suspended from a position on the central portion, which position is on a line perpendicular from the center of a line between the enters of said earpieces.

4. The dental face bow of claim 1 wherein said face bow further comprises an orbitale pointer horizontally movably positioned on one of said legs so that said pointer may be positioned to point at the orbitale of the dental patient.

5. The dental face bow of claim 1 wherein said U-shaped spring member is a unitary structure comprising a U-shaped piece of spring steel so that the terminal portions of said legs can be easily manually moved apart.

6. The dental face bow of claim 3 wherein the adjusting means comprises:
   (a) a rigid transfer rod securely perpendicularly attached to the central portion of said U-shaped spring member by means of a rigid connecting block;
   (b) a rigid bar, essentially parallel to said central portion, adjustably rigidly connected to said transfer rod, said connection being adjustable to vary the distance between the central portion and said rigid bar;
   (c) a bite plate rod rigidly secured at one end to said bite plate and adjustably rigidly connected at the other end to the rigid bar, by means of a bite plate connector, said bite plate connector allowing adjustment of said bite plate along a line parallel to said rigid bar and allowing adjustment of said bite plate toward and away from a line connecting the centers of said earpieces.

7. The dental face bow of claim 1 wherein the vertical cross sectional axis is at least four times the length of the horizontal cross sectional axis.

* * * * *